Nov. 5, 1974 J. T. IRWIN Plant Pat. 3,646
KALANCHOE PLANT
Filed Oct. 11, 1973
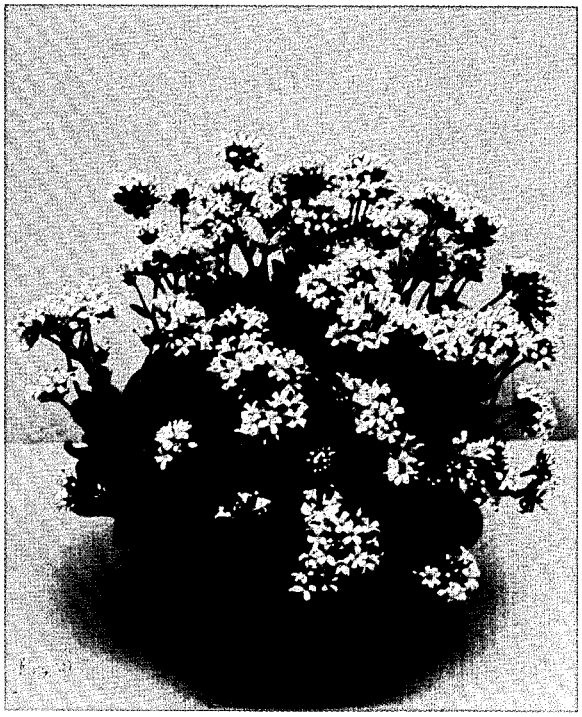
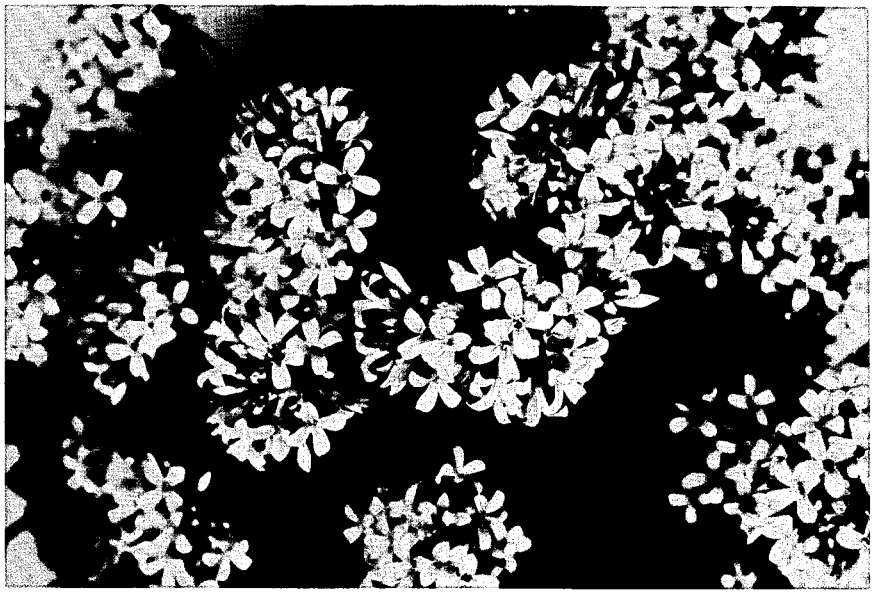

United States Patent Office

Plant Pat. 3,646
Patented Nov. 5, 1974

3,646

KALANCHOE PLANT

James T. Irwin, Canyon, Tex., assignor to J and L Plants, Incorporated, Canyon, Tex.

Filed Oct. 11, 1973, Ser. No. 405,493
Int. Cl. A01h *5/00*
U.S. Cl. Plt.—68 1 Claim

The present invention relates to a new and distinct variety of kalanchoe plant which was discovered by me as a cultivated sport of the kalanchoe variety known as "Jean" (Plant Patent No. 3,204), said discovery having been made by me in test plots being grown under my direction and supervision in my nursery located at Canyon, Texas.

At the time of my discovery, my attention was attracted to one particular plant in one of the test plots aforesaid, which appeared to be bearing flowers of a light pink color distinctly different from the normal rose color of the "Jean" variety. Closer inspection of this plant showed that the light pink flowers were borne on only one branch which apparently had sported from the plant, so I carefully preserved the sport and continued to observe the same. In due course, I asexually reproduced the sport by stem tip cuttings, as performed by me in my Canyon, Texas greenhouses. During my continued observations of the original sport and the progeny derived therefrom by the asexual propagations aforesaid, I found other distinctive differences from the "Jean" variety which convinced me that the sport was definitely a new and distinct variety, as evidenced by the following unique combination of characteristics which are outstanding therein and which distinguish this sport from its parent, as well as from all other kalanchoe varieties of which I am aware:

(1) A highly self-branching, sturdy and compact habit of growth, but being more upright and less spreading, and looser or more open than the habit of "Jean";

(2) Dense, compact and attractive foliage;

(3) A larger individual flower size, with a compact flowering tendency;

(4) A distinctive and attractive light pink flower color;

(5) A uniform blooming response and uniform blooming height ranging from about 10 to 12 inches;

(6) The ability to respond to photo-periodic changes, with consequent ability to be brought into bloom all year around;

(7) The ability to initiate and develop flower buds under high night temperatures when other varieties stall; and (8) The ability to withstand northern winters better than most hybrid kalanchoe varieties.

The accompanying drawing shows a typical blooming plant specimen of my new variety, as well as some of the blooms on a larger scale than in the view of the whole plant, as depicted in color as nearly true as it is reasonably possible to make the same in a color illustration of this character.

The following is a detailed description of my new kalanchoe variety, with color terminology in accordance with the Exotica Horticultural Color Guide, published by Roehrs Company, except where general color terms of ordinary dictionary significance are obvious:

Parentage: Sport of kalanchoe variety known as "Jean."

Propagation: Holds its distinguishing characteristics through succeeding propagations by direct rooting of stem tip cuttings.

Locality Where Grown and Observed: Randall County, Texas.

Plant:

*Form.*—Bush; much-branched; compact.

*Growth habit.*—Meduim vigor; branching; compact.

*Rooting habit.*—Roots in 10 to 14 days from any part of stem; numerous fibrous roots.

*Blooming habit.*—Compound umbel.

*Blooming season.*—Normally between about December 1 to December 15, but is photo-periodic flowering under short days and vegetative under long days; can be brought into bloom all year around.

Foliage:

*Size.*—Small.

*Quantity.*—Abundant.

*Color.*—New foliage: Upper side—Fern Green, No. 83. Under side—Fern Green, No. 83—. Old foliage: Upper side—Fern Green, No. 83. Under side—Fern Green, No. 83—; margins and under side will etch purplish under high light and cool conditions.

*Shape.*—Obovate. Tip—Obtuse. Base—From acute to obtuse.

*Texture.*—Upper side—Glossy; smooth. Under side—Smooth.

*Margin.*—Crenate.

Disease Resistance: More resistant to root rot than most kalanchoe varieties in present day commercial production, as determined by comparison with other varieties grown under the same greenhouse conditions in Randall County, Texas.

Flowers: Complete.

*Diameter.*—About 13/16 inch; averages about 23% wider than parent when grown under identical conditions.

*Depth.*—About 5/8 inch; averages about 17% longer than parent when grown under identical conditions.

*Petals.*—Length—about 11/32 inch. Width—About 3/16 inch.

*Form.*—Perigynous; 4-parted calyx, corolla and pistil; 8 stamens; section petals united; ovary inferior.

*Color.*—Upper side: Newly open—Rose Pink No. 37+. Older petals—Rose Pink, No. 37. Under side: Newly open—Rose pink, 37—. Older petals—Rose Pink, No. 37.

*Blooming period.*—From about 3 to 6 weeks.

Hardiness: Satisfactory withstands temperatures as high as 105° F. to 110° F. and as low as around 40° F., as observed in greenhouses at Canyon, Texas.

General Observations: The new sport is notable and outstanding for its short, compact growth, topped with numerous short flowering stems and which bear hundreds of individual light pink flowers (about one full shade lighter than parent when viewed in natural light) that open over a long period of time and which maintain their attractiveness for 3 to 6 weeks; the plants finish best under high light conditions in the greenhouse, or under artifiicial light in the home; under high light and cool temperatures, the foliage tends to curl upward and take on a wine colored etching on the undersides; and the new sport is also more adaptable to dark conditions of northern winters than other hybrid types of kalanchoe plants.

I claim:

1. A new and distinct variety of kalanchoe plant, substantially as herein shown and described, characterized particularly as to novelty by the unique combination of a highly self-branching, sturdy and compact habit of growth, but being more upright and less spreading and looser or more open than the habit of "Jean," dense, compact and attractive foliage, a larger individual flower size, with a compact flower tendency, a distinctive and attractive light pink flower color, a uniform blooming response and uniform blooming height ranging from about 10 to 12 inches, the ability to respond to photo-periodic changes, with consequent ability to be brought into bloom all year around, the ability to initiate and develop flower buds under high night temperatures when other varieties stall, and the ability to withstand northern winters better than most hybrid kalanchoe varieties.

References Cited

UNITED STATES PATENTS

P.P. 3,204 5/1972 Irwin ---------- Plants—68

ROBERT E. BAGWILL, Primary Examiner